(12) United States Patent
Hasson et al.

(10) Patent No.: US 11,839,429 B2
(45) Date of Patent: Dec. 12, 2023

(54) SYSTEM AND PROCESS FOR THE QUANTIFICATION OF OCULAR DOMINANCE

(71) Applicant: VISIONBALANCE TECH SRL, Trento (IT)

(72) Inventors: Uri Hasson, Trento (IT); Giuseppe Notaro, Trento (IT); Valeria D'Andrea, Trento (IT)

(73) Assignee: VISIONBALANCE TECH SRL, Trento (IT)

( * ) Notice: Subject to any disclaimer, the term of this patent is extended or adjusted under 35 U.S.C. 154(b) by 0 days.

(21) Appl. No.: 18/040,913

(22) PCT Filed: Sep. 9, 2021

(86) PCT No.: PCT/IT2021/050276
§ 371 (c)(1),
(2) Date: Feb. 7, 2023

(87) PCT Pub. No.: WO2022/059041
PCT Pub. Date: Mar. 24, 2022

(65) Prior Publication Data
US 2023/0233074 A1 Jul. 27, 2023

(30) Foreign Application Priority Data

Sep. 18, 2020 (IT) .................. 102020000022120

(51) Int. Cl.
*A61B 3/032* (2006.01)
*A61B 3/08* (2006.01)

(52) U.S. Cl.
CPC .............. *A61B 3/032* (2013.01); *A61B 3/08* (2013.01)

(58) Field of Classification Search
CPC .................................. A61B 3/032; A61B 3/08
(Continued)

(56) References Cited

U.S. PATENT DOCUMENTS 7,946,707 B1 * 5/2011 McDonald, II ........ A61B 3/032
351/203
9,345,400 B1 * 5/2016 Benefield ................ A61B 3/08
(Continued)

FOREIGN PATENT DOCUMENTS

KR 10-2020-0093926 A 8/2020

OTHER PUBLICATIONS

International Search Report of PCT/IT2021/050276 dated Nov. 30, 2021 [PCT/ISA/210].
(Continued)

*Primary Examiner* — Mohammed A Hasan
(74) *Attorney, Agent, or Firm* — Workman Nydegger

(57) ABSTRACT

A system (1) for the quantification of ocular dominance is described, comprising acquisition means (3) of graphic elements, a target element (5) disposed at a first distance (D1) from the acquisition means (3), tracking means (4) operatively cooperating with the acquisition means (3) to acquire the graphic elements, the tracking means (4) being provided to allow at least one user placed at a second distance (D2) from the acquisition means (3) to trace and represent on the acquisition medium (3) such graphic elements, the system further comprising processing means provided for quantifying the dominance eyepiece of the user; a process for quantifying ocular dominance by means of the above system (1) is also described.

15 Claims, 2 Drawing Sheets

Figure 1:
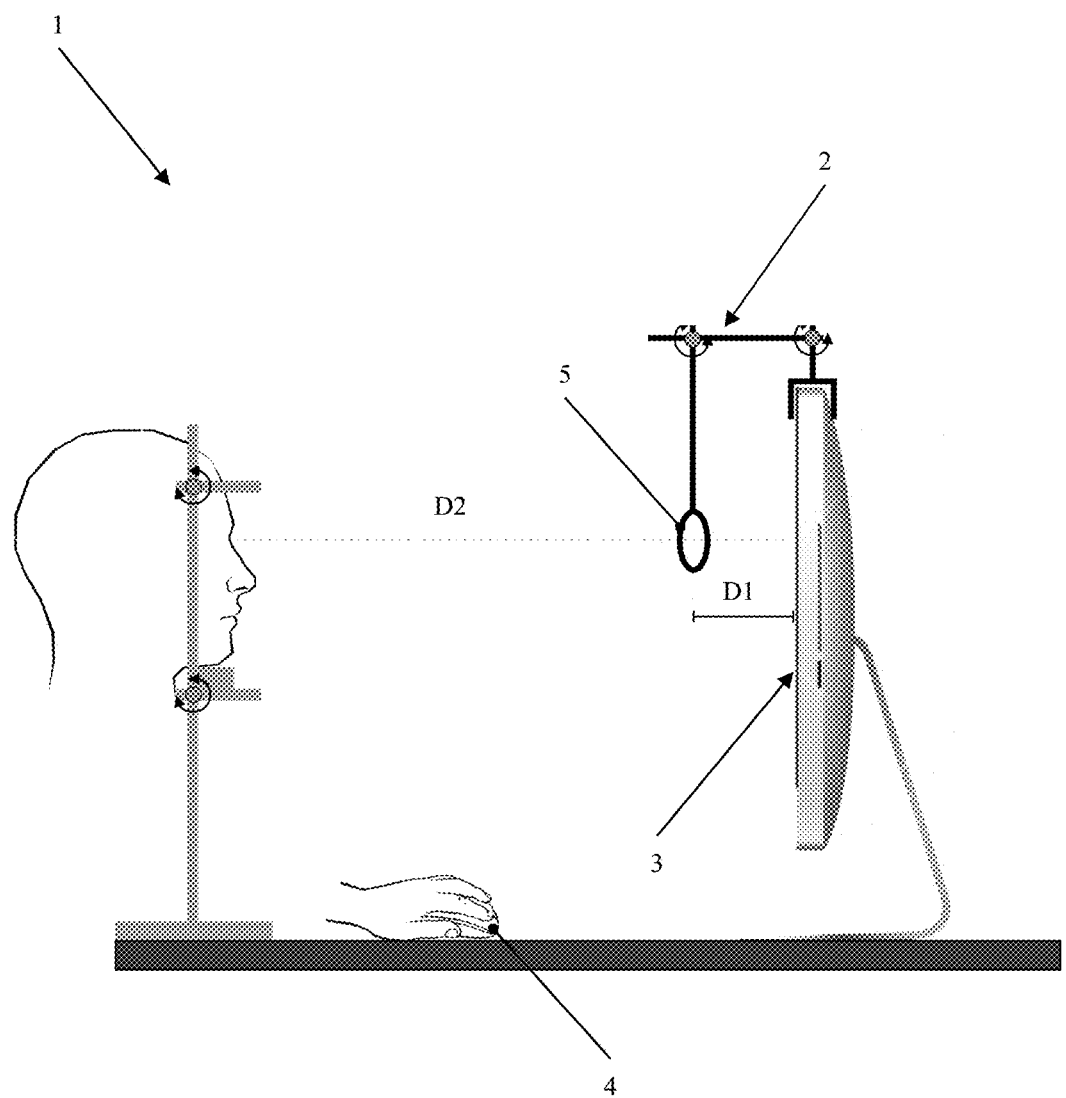

(58) Field of Classification Search
USPC .......................................................... 351/239
See application file for complete search history.

(56) References Cited

U.S. PATENT DOCUMENTS

| | | | |
|---|---|---|---|
| 2006/0287069 A1* | 12/2006 | Walker | G07F 17/3237 463/25 |
| 2009/0312817 A1* | 12/2009 | Hogle | A61B 5/682 607/54 |
| 2012/0320047 A1 | 12/2012 | Yanagita | |
| 2014/0016090 A1 | 1/2014 | Bonnin et al. | |
| 2014/0098343 A1 | 4/2014 | Haddadi | |
| 2016/0287069 A1 | 10/2016 | Haddadi | |

OTHER PUBLICATIONS

Written opinion of PCT/IT2021/050276 dated Nov. 30, 2021 [PCT/ISA/237].

* cited by examiner

SYSTEM AND PROCESS FOR THE QUANTIFICATION OF OCULAR DOMINANCE

CROSS REFERENCE TO RELATED APPLICATIONS

This application is a National Stage of International Application No. PCT/IT2021/050276 filed on Sep. 9, 2021, claiming priority based on Italian Patent Application No. 102020000022120 filed on Sep. 18, 2020, the entire disclosures of which are incorporated herein by reference.

The present invention refers to a system and a process for the quantification of ocular dominance. Many empirical studies in basic and applied contexts require the analysis of the metrics of eye movements, such as the latencies of the saccades to the sets of stimuli or the position and duration of fixations. As a preliminary stage, these studies require the identification of the subject's dominant eye. For simplicity, often only the activity of one eye is recorded, assuming a perfect left/right symmetry of the attentional space of the subjects and the measured metrics of the eye. Very often, researchers claim to record the dominant eye, assuming that, even in the absence of such symmetries, the measurements of the dominant eye are the most relevant from a behavioural point of view. Moreover, the measurement of the eye dominance can allow personalization of corrective glasses and of refractiveness surgical plans.

However, there is a lack of methods to correctly quantify the dominance of an eye, the few existing methods giving mixed results, and none of them relying on an explicit model of binocular vision.

In particular, known art mainly describes the following methods:
- method of measuring the ocular dominance through the comparison of the monocular detection thresholds of moving points with random direction; this method involves processing the perception of movement;
- method of measuring the ocular domain by measuring the temporal duration in which a visual percept reflects input exclusively perceived through each of the eyes, using a stimulus that arouses binocular rivalry. Because the method is based on a habituation effect that develops over time, it is not clear whether the measure effect is due to dominance in sampling visual space (perception) or dominance in attending to parts of space over long time periods (attention). Moreover, the measure can be highly dependent on the stimulus properties;
- method of characterization of the ocular domain through the peak velocity of goal-directed directional saccades. This measure requires that the subject integrates the visual features of a target, plans and execute an eye movement to the target, and also requires the availability of an eye-tracker;
- method based on bisection of a straight line, to measure a spatial distortion in spatial attention linked to ocular dominance;
- Hess-Lancaster method for the clinical evaluation of ocular misalignment;
- methods based on the measure of the target displacement made by a subject that holds it in his hands and want to view it in monocular conditions.

The object of the present invention is solving the aforementioned prior art problems by providing a fast and inexpensive, reliable system and process for the quantification of ocular dominance which directly quantifies the contribution to low-level ocular domain, as its measurements depend only on the weights of sensory inputs (without tapping into higher-level-non-sensory-factors such as visual attention), as opposed to other high-level attentional contributions.

In general, known methods for quantifying ocular dominance are either less sensitive, based on heuristics rather than a quantitative model, based on subjective perceptions, or measure the effect of higher-level factors (non-sensory, such as visual attention) that affect dominance.

The aforementioned and other objects and advantages of the invention, which will emerge from the following description, are achieved with a system and a process such as those described in the respective independent claims. Preferred embodiments and non-trivial variants of the present invention form the subject matter of the dependent claims.

It is understood that all attached claims form an integral part of the present description.

It will be immediately obvious that numerous variations and modifications (for example relating to shape, dimensions, arrangements and parts with equivalent functionality) can be made to what is described, without departing from the scope of the invention as appears from the attached claims.

Figure 2:
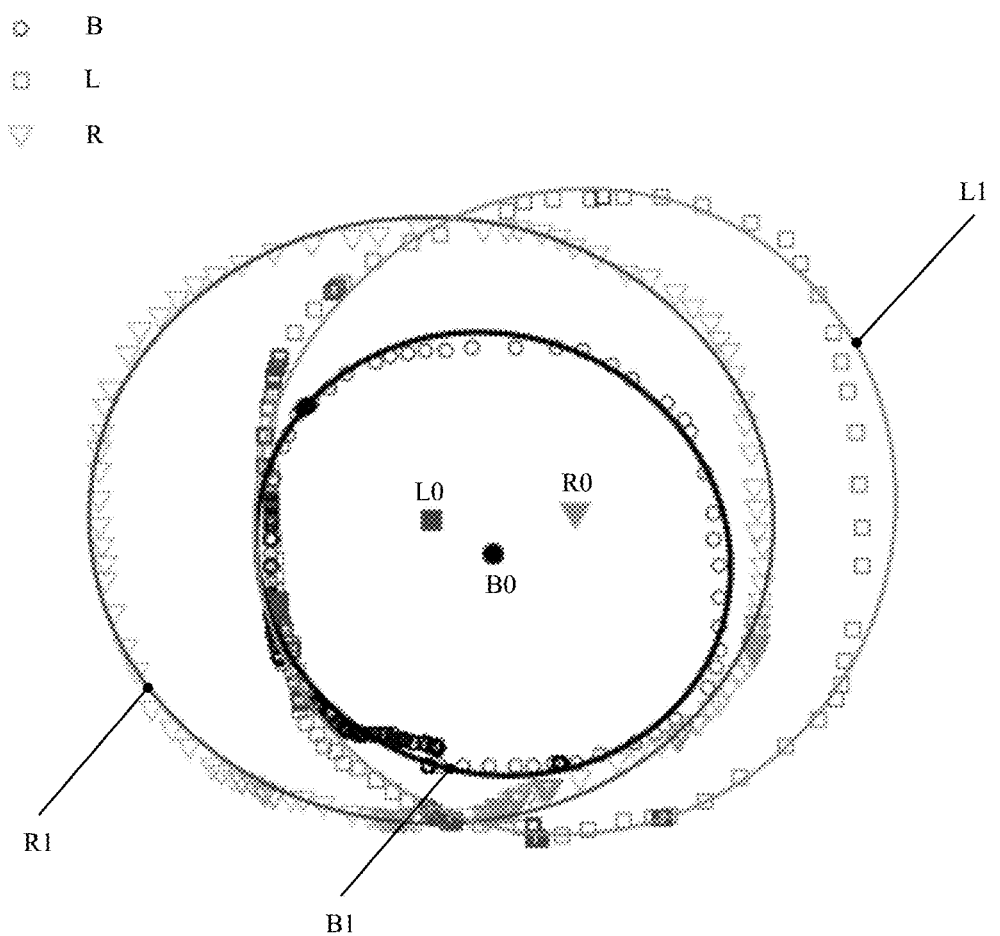

The present invention will be better described by some preferred embodiments, provided by way of non-limiting example, with reference to the attached drawings, in which:

FIG. 1 shows a schematic representation of a preferred embodiment of the system according to the present invention; and FIG. 2 shows a schematic representation of an example of data detected using the method according to the present invention.

In general, as will be seen in greater detail below, the system and the process according to the invention are provided to identify the dominant eye of a user using a measurement based on a simple mechanistic model of binocular vision. In this model, each eye provides the visual system with an input similar to that obtained from a pinhole camera. In the binocular fusion process, the two eye inputs are weighted to obtain a unique image of the world. The eye that contributes a heavier weight is considered to be the dominant one.

In particular, the main idea of the system and of the method according to the present invention is to project on acquisition means (like a monitor screen) the monocular views of a simple object, such as a disk, as perceived by each eye when used alone. These projections are then quantitatively compared with the projection of the object obtained under a binocular-viewing condition. This produces a highly reliable measurement that directly reflects the person's perception of the world in one or both eyes.

With reference therefore in particular to FIG. 1, it is possible to note that the system 1 for quantifying the ocular dominance according to the present invention comprises at least one means for acquiring and optionally displaying at least graphic elements 3, at least one target element 5 arranged at a first distance D1 from said acquisition means 3, at least one tracing means 4 operatively cooperating with said acquisition means to acquire said graphic elements, said tracing means 4 being provided to allow at least one user of said system placed at a second distance D2 from said target element 5 to represent on the acquisition means 3 these graphic elements in the form of at least a first contour B of this target element 5 when said target element 5 is sighted by both eyes open of said user (binocular condition), at least a second contour L of such target element 5 when said target element 5 itself is sighted by only one LEFT eye of that user (first monocular condition), and at least a third contour R of said target element 5 when said target element 5 itself is sighted by only the RIGHT eye of that user (second monocular condition), said system further comprising processing means provided for comparing said contours drawn by said user on said acquisition means 3 by means of such tracing means 4 and quantifying the ocular dominance of said user as a function of the level of overlap between said contours.

Preferably, this acquisition means 3 can be a computer monitor and this tracking means 4 can be a mouse, these contours being able to be graphically represented on this acquisition means 3 by means of the mouse pointer 4 displayed on that monitor.

Preferably, this target element 5 is a circular element, possibly provided with a suitable support 2.

Preferably, this first distance D1 is substantially equal to 5 cm, this second distance D2 is substantially equal to 60 cm, and preferably corresponds to the distance of the user's eyes from the acquisition means 3, and the target, if circular, 5 has a diameter substantially equal to 5 cm.

With different tracing and acquisition means, our system can measure the ocular dominance at different distance D2 between the subject and the target. For example the second distance D2 can be about 3-4 meters, the target diameter can be about 30 cm, and means to detect positions (like a video camera o Kinect; acquisition means) can record the position of the subject's finger or a pointer (tracing means) moving around the contour of the target in the different conditions (binocular and monocular). As another embodiment, the method could be implemented in a Virtual Reality environment, making possible the measure of the ocular dominance at any distance D2.

Optionally, it is possible to provide that the system 1 according to the present invention also includes a system, for example by videography to check that the subject's head is parallel and aligned with the target before each trial, and include correction algorithms, to correct the fluctuations due to the small movements of the user's head.

The present invention also relates to a process for quantifying ocular dominance by means of a system 1 such as the one described above. In particular, the process according to the present invention comprises the following steps:
- a step in which the user traces, by means of said at least one tracing means 4, the contour B (line represented with a plurality of circles in FIG. 2) of the target element 5 in binocular condition (sighted by both eyes naturally open);
- a step in which the user traces, by means of said at least one tracing means 4, the contour L (line represented with a plurality of squares in FIG. 2) of the target element 5 in a monocular condition seen by only one eye (left eye in the example);
- a step in which the user traces, by means of said at least one tracing means 4, the contour R (line represented with a plurality of triangles in FIG. 2) of the target element 5 in a monocular condition seen only by the other eye (right eye in the example);
- a step in which, for each traced contour, an ellipse shape B1, L1, R1 is estimated (continued in FIG. 2) and the centre B0, L0, R0 of each ellipse B1, L1, R1 is calculated;
- an optional step in which some repetitions of the tracing are performed in each condition;
- a step in which the average of the difference between the distances of the pairs of centres B0, L0, R0 (DR right eye vs binocular; DL left eye vs binocular) is calculated to quantify the ODscore ocular dominance, using formula:

$$OD_{score} = \frac{DL - |DR|}{DL + |DR|}$$

We note that the weight of the monocular contributions to binocular vision behind our model can be expressed by alternative mathematical quantifications (i.e the ratio between the ellipse areas).

Preferably, the process for quantifying the ocular dominance according to the invention also includes algorithms to check for the alignment between the subject's head and the target and to correct the error due to the small movements of the user's head.

Advantageously, the system and the method allow to correct for an eventual dominant eye. To this end it is necessary to put glasses with a neutral filter lens in front of the dominant eye and decrease the percentage of transmitted light of the neutral filter, until the measured dominance score (ODscore), as defined e.g. in the above formula, is zero.

Advantageously, the system and the method according to the invention allow, in applied research, to increase the sensitivity of the ocular dominance measurement and its validity. This is crucial, for example, in the selection of personnel for particular positions (e.g. fighter pilots) or in the design of Head-Up Displays (UHDs) for particular sectors. The system according to the invention also has application in the fields of computer vision where the engineering objective is to build a model (using a neural network) of what the human viewer is perceiving. This, for example, is one of the main objectives of AI-based systems that help in semi-autonomous driving. Allowing these systems to better understand which visual input is dominant will improve their effectiveness and ultimately their safety.

Furthermore, the system and method according to the invention are relevant to basic research, where they have the potential to become a standard evaluation to be performed prior to any study of visual perception. Indeed, the sensory ocular domain may be a relevant covariate of ocular metrics and electro-physiological recordings. For this reason, the system according to the present invention can be sold for example by eye-tracker manufacturers as a complementary tool.

Finally, in the clinical setting, the system and the method according to the present invention can be used in the clinical diagnosis of amblyopia, glaucoma in the initial step or strabismus.

The invention claimed is:

1. A system for the quantification of ocular dominance comprising:
   - at least one acquisition means for acquisition of at least graphic elements,
   - at least one target element positioned at a first distance from said at least one acquisition means of at least graphic elements, and
   - at least one tracking means spaced apart and operatively cooperating with said at least one acquisition means to acquire said graphic elements, said at least one tracking means configured to allow at least one user of said at least one tracking means placed at a second distance (D2) from said target element to represent on the at least one acquisition means such graphic elements, this at least one tracking means being configured to allow said at least one user to draw and represent on the at least one acquisition means such graphic elements in the form of at least one first outline (B) of such target element when said target element itself is sighted by both the eyes of such user spaced from it, at least one second contour (L) of such target element when such target element itself is sighted by only one eye of said user, and at least one third contour (R) of said target element when said target element itself is sighted by only the other eye of said user, said processing means being configured to compare said contours traced by such user on such at least one acquisition means by means of such at least one tracking means and quantify the ocular dominance of that user as a function of the level of overlap between such contours, and said processing means being configured to compare the first, second and third contours (B, L, R) to quantify the ocular dominance of this user.

2. The system for the quantification of ocular dominance according to claim 1, wherein said at least one acquisition means are a computer monitor and such at least one tracking means are a mouse, said contours being graphically represented on this acquisition means by means of the mouse pointer displayed on this monitor.

3. The system for the quantification of ocular dominance according to claim 1, wherein said target element is a circular element.

4. The system for the quantification of ocular dominance according to claim 1, wherein said first distance (D1) is equal to 5 cm, said second distance (D2) is equal to 60 cm and said element circular has a diameter equal to 5 cm.

5. The system for the quantification of ocular dominance according to claim 1, wherein the at least one acquisition means are means for detecting positions, and the at least one tracking means are a subject's finger or a pointer.

6. The system for the quantification of ocular dominance according to claim 1, further comprising a system for reducing fluctuations due to small movements of the user's head.

7. A process for quantifying ocular dominance by means of the system according to claim 1, comprising the following steps:
- a step in which the user traces through said at least one tracing means the contour (B) of the target element in a binocular condition;
- a step in which the user traces by means of said at least one tracing means the contour (L) of the target element in a monocular condition where the observation is made by only one eye;
- a step in which the user traces by means of said at least one tracing means the contour (R) of the target element in a monocular condition where observation is made only by the other eye;
- a step in which an ellipse shape (B1, L1, R1) is made for each contour drawn and the center (B0, L0, R0) of each ellipse (B1, L1, R1) is calculated;
- an optional step in which some repetitions of the tracing are performed in each condition; and
- a step in which the average of the difference between the distances of the pairs of centers (B0, L0, R0) is calculated.

8. The process for quantifying ocular dominance according to claim 7, wherein the average of the difference between the distances of the pairs of centers (B0, L0, R0) is calculated using formula:

$$ODscore = DL - |DR|/DL + |DR|$$

where DR is the distance between the center of the ellipse drawn in the monocular condition with the right eye and the center of the ellipse drawn in the binocular condition and DL is the distance between the center of the ellipse drawn in the monocular condition with the left eye and the center of the ellipse drawn in binocular condition.

9. The process for quantifying ocular dominance according to claim 7, further comprising an algorithm to correct the error due to small movements of the user's head.

10. The process for quantifying ocular dominance according to claim 7, further comprising a step of putting glasses with a neutral filter lens in front of the dominant eye and decrease the percentage of transmitted light of the neutral filter, until the measured dominance score is zero in order to correct for an eventual dominant eye.

11. A process for quantifying ocular dominance by means of the system according to claim 2, comprising the following steps:
- a step in which the user traces through said at least one tracing means the contour (B) of the target element in a binocular condition;
- a step in which the user traces by means of said at least one tracing means the contour (L) of the target element in a monocular condition where the observation is made by only one eye;
- a step in which the user traces by means of said at least one tracing means the contour (R) of the target element in a monocular condition where observation is made only by the other eye;
- a step in which an ellipse shape (B1, L1, R1) is made for each contour drawn and the center (B0, L0, R0) of each ellipse (B1, L1, R1) is calculated;
- an optional step in which some repetitions of the tracing are performed in each condition; and
- a step in which the average of the difference between the distances of the pairs of centers (B0, L0, R0) is calculated.

12. A process for quantifying ocular dominance by means of the system according to claim 3, comprising the following steps:
- a step in which the user traces through said at least one tracing means the contour (B) of the target element in a binocular condition;
- a step in which the user traces by means of said at least one tracing means the contour (L) of the target element in a monocular condition where the observation is made by only one eye;
- a step in which the user traces by means of said at least one tracing means the contour (R) of the target element in a monocular condition where observation is made only by the other eye;
- a step in which an ellipse shape (B1, L1, R1) is made for each contour drawn and the center (B0, L0, R0) of each ellipse (B1, L1, R1) is calculated;
- an optional step in which some repetitions of the tracing are performed in each condition; and
- a step in which the average of the difference between the distances of the pairs of centers (B0, L0, R0) is calculated.

13. A process for quantifying ocular dominance by means of the system according to claim 4, comprising the following steps:
- a step in which the user traces through said at least one tracing means the contour (B) of the target element in a binocular condition;
- a step in which the user traces by means of said at least one tracing means the contour (L) of the target element in a monocular condition where the observation is made by only one eye;

a step in which the user traces by means of said at least one tracing means the contour (R) of the target element in a monocular condition where observation is made only by the other eye;

a step in which an ellipse shape (B1, L1, R1) is made for each contour drawn and the center (B0, L0, R0) of each ellipse (B1, L1, R1) is calculated;

an optional step in which some repetitions of the tracing are performed in each condition; and a step in which the average of the difference between the distances of the pairs of centers (B0, L0, R0) is calculated.

14. A process for quantifying ocular dominance by means of the system according to claim 5, comprising the following steps:

a step in which the user traces through said at least one tracing means the contour (B) of the target element in a binocular condition;

a step in which the user traces by means of said at least one tracing means the contour (L) of the target element in a monocular condition where the observation is made by only one eye;

a step in which the user traces by means of said at least one tracing means the contour (R) of the target element in a monocular condition where observation is made only by the other eye;

a step in which an ellipse shape (B1, L1, R1) is made for each contour drawn and the center (B0, L0, R0) of each ellipse (B1, L1, R1) is calculated;

an optional step in which some repetitions of the tracing are performed in each condition; and a step in which the average of the difference between the distances of the pairs of centers (B0, L0, R0) is calculated.

15. A process for quantifying ocular dominance by means of the system according to claim 6, comprising the following steps:

a step in which the user traces through said at least one tracing means the contour (B) of the target element in a binocular condition;

a step in which the user traces by means of said at least one tracing means the contour (L) of the target element in a monocular condition where the observation is made by only one eye;

a step in which the user traces by means of said at least one tracing means the contour (R) of the target element in a monocular condition where observation is made only by the other eye;

a step in which an ellipse shape (B1, L1, R1) is made for each contour drawn and the center (B0, L0, R0) of each ellipse (B1, L1, R1) is calculated;

an optional step in which some repetitions of the tracing are performed in each condition; and a step in which the average of the difference between the distances of the pairs of centers (B0, L0, R0) is calculated.

* * * * *